(12) United States Patent
Reheulishvili et al.

(10) Patent No.: US 7,148,068 B1
(45) Date of Patent: Dec. 12, 2006

(54) METHOD OF TRIVALENT CHROMIUM CONCENTRATION DETERMINATION BY ATOMIC SPECTROMETRY

(76) Inventors: Aleksandre N. Reheulishvili, Nutsubidze Plato, microarea 2, Block 3, Building 3, apt. 21, Tbilisi, 0183 (GE); Neli Ya. Tsibakhashvili, 14 Salkhino Str., Tbilisi, 0101 (GE)

(*) Notice: Subject to any disclaimer, the term of this patent is extended or adjusted under 35 U.S.C. 154(b) by 800 days.

(21) Appl. No.: 10/403,296

(22) Filed: Apr. 1, 2003

(51) Int. Cl.
*G01N 33/20* (2006.01)
*G01N 33/48* (2006.01)

(52) U.S. Cl. .............................. 436/83; 436/74; 436/53

(58) Field of Classification Search .................. 436/83, 436/74, 63
See application file for complete search history.

(56) References Cited

OTHER PUBLICATIONS

Reheulishvili A.N., Tsibakhashvili G.G. and Kaadze K.D., The Effect of the Chromium Valent State on the Results of Atomic Absorption and Atomic Fluorescent Spectroscopy of Chromium, (2001), Georgian Engineering News, 1, 118-122.
A. Reheulishvilli et al, Determination of the Content of Cr(VI) by the Method of Flame Atomic Absorption and Atomic Fluorescent Spectrometry (2002), Bulletin of the Georgian Academy of Sciences, 3, 501-504.
J. Posta, A. Gaspar, R. Toth, L. Ombodi, Cr(III) and Cr(VI) On-Line Preconcentration and High-Performance Flow Flame Emission Spectrometric Determination in Water Samples, (1996). Microchemical J., 54, 195-203.
J. Posta, A. Gaspar, T. Toth, L. Ombodi, Cr(III) and Cr(VI) On-Line Preconcentration and Determination with High Performance Flow Flame Emission Spectrometry in Natural Samples, (1996) Fresenius J. Anal. Chem, 355, 719-720.
A. Gaspar, J. Posta, On-line Sorption Preconcentration of Chromium(VI) and its Determination by Flame Atomic Absorption Spectrometry, (1997), Analitica Chimica Acta, 354, 151-158.
S. Tokahoglu, S. Kartal, L. Elci, Determination of Trace Metals in Waters by FAAS after Enrichment as Metal-HMDTC Complexes using Solid Phase Extraction, Bull. Korean Chem. Soc. (2002), vol. 23, No. 5, 693-698.
C. Sogor, A. Gaspar, J. Posta, Flame Atomic Absorption Spectrometric Determination of Total Chromium and Cr(VI) in Cigarette Ash and Smoke using Flow Injection/Hydraulic High-Pressure Sample Introduction, (1998), Microchemical Journal 58, 251-255.
A. Gaspar, S. Sogor, J. Posta, Possibilities for the simultaneous preconcentration and flame atomic absorption spectrometric determination of Cr(III) and Cr(VI) using a C18 column and sorption loop, (1999), Fresenius J. Anal. Chem., 363, 480.
A. Gaspar, J. Posta, R. Toth, On-line Chromatographic Separation and Determination of Chromium(III) and Chromium(VI) with Preconcentration of the Chromium(III) using Potassium Hydrogen Phtalate, in Various Samples by Flame Atomic Absorption Spectrometry, (1996), J. Anal. Atom. Spectrosc. vol. 11, 1067-1074.
J.Posta, A. Alimonti, F. Petrucci, S. Caroli, On-Line Separation and Preconcentration of Chromium Species in Seawater, (1996), Analytica Chimica Acta, 325, pp. 185-193.
Technical Report of the 8th Quarter—Project G-348, issued Sep. 30, 2002.

*Primary Examiner*—Jill Warden
*Assistant Examiner*—Keri Moss
(74) *Attorney, Agent, or Firm*—John T. Lucas; Paul A. Gottlieb

(57) ABSTRACT

A method is disclosed for determining the concentration of trivalent chromium Cr(III) in a sample. The addition of perchloric acid has been found to increase the atomic chromium spectrometric signal due to Cr(III), while leaving the signal due to hexavalent chromium Cr(VI) unchanged. This enables determination of the Cr(III) concentration without pre-concentration or pre-separation from chromium of other valences. The Cr(III) concentration may be measured using atomic absorption spectrometry, atomic emission spectrometry or atomic fluorescence spectrometry.

19 Claims, 3 Drawing Sheets

METHOD OF TRIVALENT CHROMIUM CONCENTRATION DETERMINATION BY ATOMIC SPECTROMETRY

STATEMENT OF GOVERNMENT INTEREST

None

CROSS-REFERENCE TO RELATED APPLICATIONS

None

BACKGROUND OF THE INVENTION

The present invention relates generally to a method of detecting trivalent chromium Cr(III), and particularly to a method of detection using atomic spectrometric methods without pre-concentration or preliminary separation from chromium in other valence states.

The chemical speciation of trace elements in samples is very important because their chemical forms generally influence the effects that such trace elements (especially trace heavy metals) have on ecological and environmental systems. Some elements in a sample may be present in more than one valence state, as well as cationic, anionic and neutral species. The increasing demand for speciation information from a particular sample arises from the understanding that the toxicity of a given element critically depends on its actual present chemical form. The different oxidation states of chromium is of critical concern. Trivalent chromium Cr(III) is considered a trace element essential for the proper functioning of living organisms. On the other hand, hexavalent chromium Cr(VI) presents the possibility of toxic effects on biological systems.

Chromium is commonly used in various industries, and may be released in a considerable amount into the environment. Cr(VI) may be transformed into Cr(III) by various means (chemical and/or biological). Accurate speciation information would be useful in assessing the impact of releases to, the environment and the effectiveness of remediation efforts.

There are various known techniques for speciation determination of chromium, including Electron Spin Resonance (ESR) spectrometry, ion chromatography and high-performance liquid chromatography (HPLC), that are often coupled with sophisticated detection systems like inductively coupled plasma atomic emission or mass spectrometry. However, these procedures do not satisfy all requirements for routine analysis mainly because of their complicated process design, time consumption or the need for expensive instruments.

Atomic absorption spectrometry (AAS) is the key technique for the determination of total chromium. Among AAS techniques, flame atomic absorption spectrometry (FAAS) is preferred because it is simple and inexpensive. Efforts to determine trace metals directly and reliably by FAAS are usually limited owing to the low concentrations of analytes and matrix interferences. To enhance the sensitivity and the precision of the method, pre-concentration and separation techniques, such as co-precipitation, liquid—liquid phase extraction, ion exchange and recently, solid-phase extraction are most frequently used.

SUMMARY OF THE INVENTION

An object of the present invention is a method of direct detection of trivalent chromium Cr(III) without preliminary separation from chromium in other valence states.

Another object of the present invention is a method of direct detection of trivalent chromium Cr(III) without pre-concentration.

In embodiments of the present invention, perchloric acid ($HClO_4$) is added to a sample (in solution), inducing an increase in the atomic chromium spectrometric signal due to trivalent chromium Cr(III), while leaving the atomic chromium spectrometric signal due to hexavalent chromium Cr(VI) essentially unchanged. Thus concentration of Cr(III) may be determined by dividing the sample into two parts, adding an effective amount of perchloric acid (sufficient to induce an increase in chromium signal from the Cr(III) fraction) to one of the parts, preferably adding an about equal amount of preferably distilled water to the other part, measuring the atomic chromium spectrometric signals of each part, and comparing them to the spectrometric signals similarly measured for one or more standard(s) of known Cr(III) concentration(s). The atomic spectrometric signals may be measured by atomic absorption spectrometry (AAS), atomic emission spectrometry (AES) or atomic fluorescence spectrometry (AFS), all means well known in the art. In the case of AAS, the addition of perchloric acid increases the absorption at the resonance spectral line wavelengths characteristic for chromium. In the case of AES and AFS, the perchloric acid increases the intensity of the light emitted/fluoresced at the resonance spectral line wavelengths characteristic for chromium.

In the various embodiments of the present invention described, the effective amounts of perchloric acid added to the sample and calibration standard are selected to cause an increase, preferably the maximum increase, in atomic spectrometric signal. The effective amounts of perchloric acid are preferably selected from the range of 0.3 to 10%, most preferably 0.3 to 1%. Experimental measurements indicated that adding even a small amount of perchloric acid (0.3%) caused a two fold increase in chromium atomic absorption (AAS) and fluorescence (AFS) signals at a wavelength of 357.9 nm in a propane-butane-air flame. The preferred ranges of amounts of perchloric acid are based on 35% solution concentration, 4.35 molarity. If other concentrations are used, then the effective amount ranges may be adjusted by the factor (4.35/m) where m is the actual molarity.

In the various embodiments of the present invention described, the chromium absorption, emittance, and fluorescence signals are measured at wavelengths corresponding to the resonance spectral lines for chromium, preferably at a wavelength of 395.3 nm, 360.5 nm, 425.4 nm or 357.9 nm, most preferably at 357.9 nm.

DETAILED DESCRIPTION OF THE INVENTION

Definitions

Figure 1A:
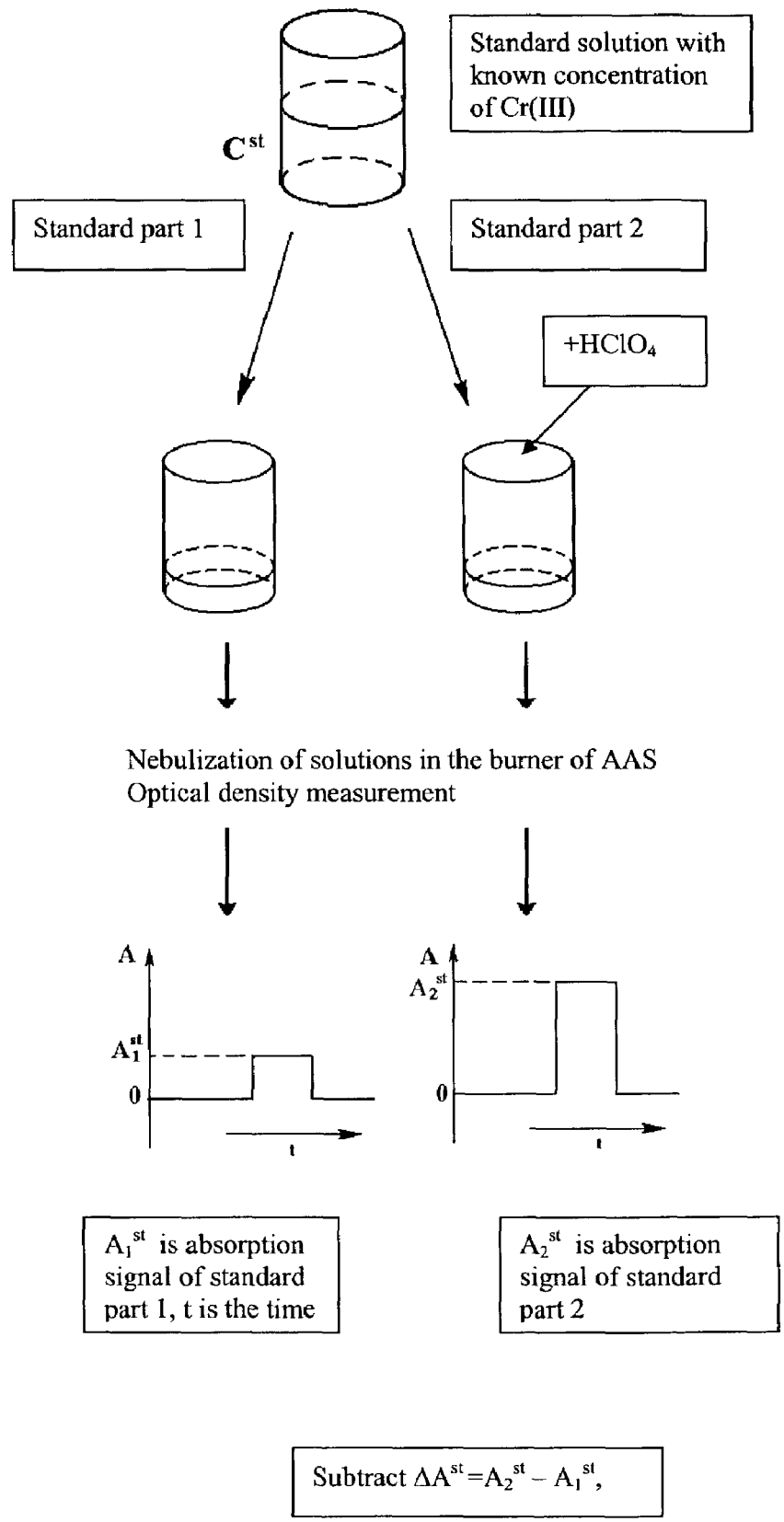
FIG. 1A illustrates the process for measurement of the absorption signals for a standard of known concentration.

Atomic Absorption Spectrometry (AAS)—determination of the concentration of an analyte by the reduction in intensity of light due to light absorbed by atomized atoms of the analyte at the atomic absorption wavelength(s) specific for that analyte. In flame atomic absorption spectrometry (FAAS), the sample (in solution) is nebulized into a flame which desolvates, volatilizes, and atomizes the analyte into elemental form. Light, from a source (such as a hollow cathode lamp) is aimed at the flame. The absorption signal (reduction in light intensity due to absorption of light by the analyte atoms causing a transition in the analyte atoms to an excited state) is measured by a detector at a wavelength characteristic for the analyte. A monochromator may be placed between the flame and the detector to allow passing only light characteristic for the analyte. Analyte concentrations can thus be determined via comparison to calibration curves based on measured absorption for known concentrations.

Atomic Emission Spectrometry (AES)—determination of the concentration of an analyte by the measurement of the intensity of emitted light at wavelengths specific for excited atoms of the analyte. In flame atomic emission spectrometry (FAES), the sample (in solution) is nebulized into a flame which desolvates, volatilizes, atomizes the analyte into elemental form and raises the elemental analyte from the ground state into an excited state. A detector measures the emittance signal (intensity of light emitted by the excited analyte atoms), at a wavelength characteristic for the analyte. A wavelength selector (such as a monochromator or polychromator) may be placed between the flame and the detector to more easily distinguish the light from the excited analyte atoms from other species that may be present in the flame. Analyte concentrations can thus be determined via comparison to calibration curves based on measured emission for known concentrations.

Atomic Fluorescence Spectrometry (AFS)—determination of the concentration of an analyte by the measurement of the intensity of fluorescent light at wavelengths specific for excited atoms of the analyte. In flame atomic fluorescence spectrometry (FAFS), the sample (in solution) is nebulized into a flame which desolvates, volatilizes, and atomizes the analyte into elemental form. The analyte atoms are raised from the ground state into an excited state by the absorption of photons from a light source, (such as a laser or hollow cathode lamp). A detector measures the fluorescence signal (intensity of fluorescent light emitted from the excited analyte atoms), at a wavelength characteristic for said analyte. A wavelength selector (such as a monochromator or polychromator) may be placed between the flame and the detector to more easily distinguish the fluorescing light from the excited analyte atoms from other species that may be present in the flame. Analyte concentrations can thus be determined via comparison to calibration curves based on measured fluorescence for known concentrations.

Atomization—process in which the analyte is converted into elemental (atomic) form.

Desolvation—process in which solvent separated from the solute.

Increased Atomic Spectrometric Signal—a) In AAS, increased absorption due to excited analyte atoms; b) In AES, increased intensity of emission from excited analyte atoms; c) In AFS, increased intensity of fluorescence from excited analyte atoms, at a characteristic wavelength for a particular analyte.

Nebulization—process of converting a solution into a fine aerosol, and in certain configurations to mix the aerosol with fuel and oxidant for introduction into a flame for atomization.

Volatilization—process to transform a material into vapor.

EMBODIMENTS OF THE INVENTION

In various embodiments of the present invention, perchloric acid ($HClO_4$) is added to a sample (in solution) in order to induce an increase in the atomic chromium spectrometric signal due to trivalent chromium Cr(III), while leaving the spectrometric signal due to hexavalent chromium Cr(VI) essentially unchanged. In preferred embodiments of the present invention, the sample is divided into two parts, and an effective amount of perchloric acid sufficient to induce an increase in trivalent chromium signal is added to one of the parts. Preferably, an about equal amount of distilled water is added to the other part to maintain equality of sample volumes. Distilled water is preferred, but other liquids may be used that are transparent at the relevant wavelengths and are chemically non-reactive with the sample constituents. The two parts are nebulized, and the chromium atomic spectrometric signals measured by flame atomic absorption spectrometry (FAAS), flame atomic emission spectrometry (FAES) or flame atomic fluorescence spectrometry (FAFS). The same process is applied to one or more standard solutions of known Cr(III) concentrations.

Figure 1B:
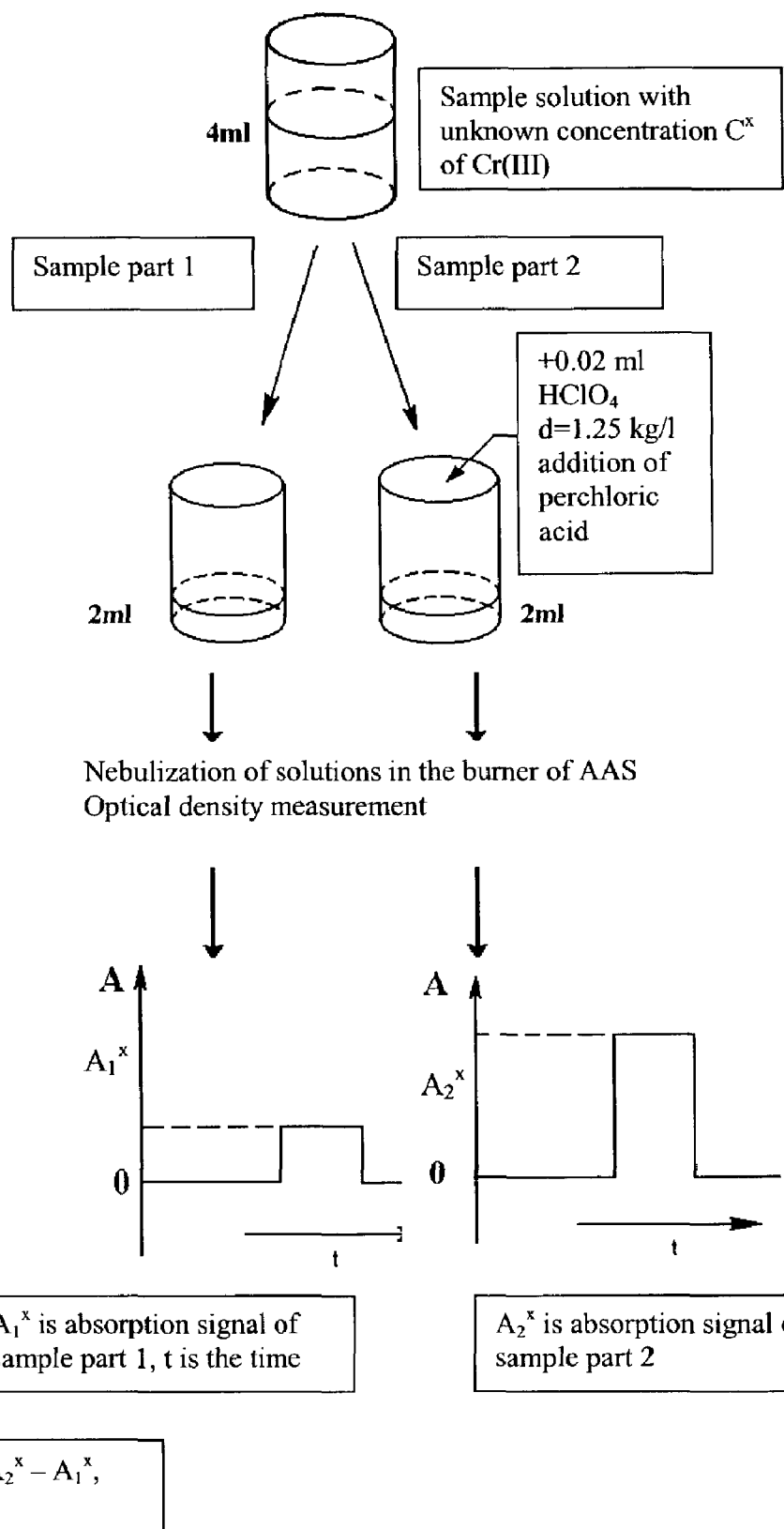
FIG. 1B illustrates the process for measurement of the absorption signals for the sample to be analyzed.
Figure 1C:
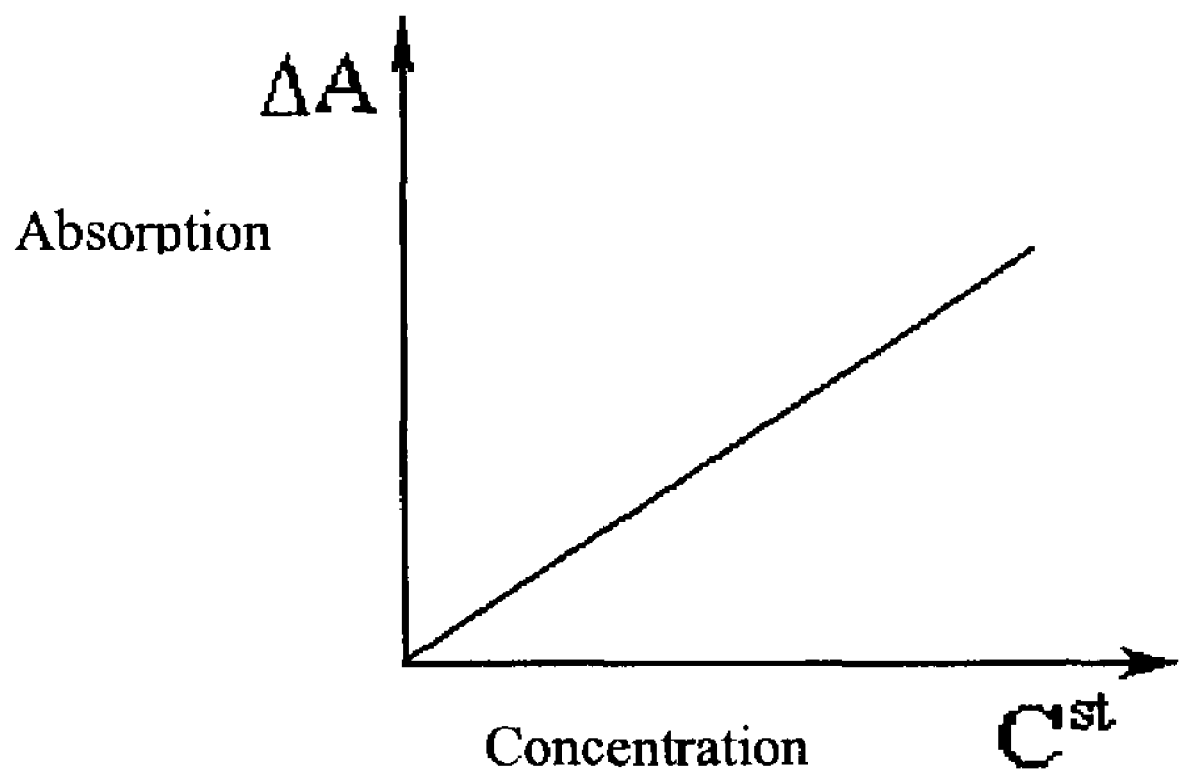
FIG. 1C illustrates a calibration curve of differences in absorption signal vs. various concentrations of perchloric acid.

In one embodiment of the present invention, the chromium atomic spectrometric signals are measured by flame atomic absorption spectrometric (FAAS) means. The flame is preferably low-temperature (such as propane-butane-air). As shown in FIG. 1A, chromium atomic absorption signals $A_1^{st}$ (without added $HClO_4$) and $A_2^{st}$ (with added $HClO_4$) are measured for the two parts of a solution of known Cr(III) concentration $C^{st}$. A calibration curve (FIG. 1C) may be generated (if measurements are made for multiple concentrations). FIG. 1B illustrates measurement of chromium atomic absorption signals $A_1^x$ (without added $HClO_4$) and $A^{2x}$ (with added $HClO_4$) for the two parts of the sample to be analyzed. The Cr(III) concentration $C^x$ may be determined from the calibration curve for the measured value of $\Delta A^x$. Alternatively, the sample Cr(III) concentration $C^x$ may be calculated from:

$$C^x/(A_2^x - A_1^x) = C^{st}/(A_2^{st} - A_1^{st})$$

In a preferred embodiment, the spectrometric absorption signal A is the absorbance (optical density OD) which is determined via the formula $OD = \log(I_O/I)$, wherein $I_O$ is the original light intensity (from the light source) and I is the transmitted light intensity. Over a certain range of concentrations, absorbance is linearly proportional to the concentration C. Preferably, calibration standards would be designed to span this linear range, allowing interpolation and extrapolation of values in this range.

In another embodiment of the present invention, the chromium atomic spectrometric signals are measured by flame atomic emission spectrometric (FAES) means. The flame is preferably low-temperature (such as propane-butane-air). In this embodiment, the flame not only serves to desolvate, volatilize, and atomize the analyte, the flame also raises the elemental chromium to an excited state. Analogous to the FAAS process shown in FIG. 1A, chromium emittance signals $E_1^{st}$ (without added $HClO_4$) and $E_2^{st}$ (with added $HClO_4$) are measured for a solution of known Cr(III) concentration $C^{st}$. A calibration curve analogous to that shown in FIG. 1C may be generated (if measurements are made for multiple concentrations). Analogous to the FAAS process shown in FIG. 1B chromium atomic emittance signals $E_1^x$ (without added $HClO_4$) and $E_2^x$ (with added $HClO_4$) are measured for the sample to be analyzed. The Cr(III) concentration $C^x$ may be determined from the calibration curve for the measured value of $\Delta E^x$. Alternatively, the sample Cr(III) concentration $C^x$ may be calculated from:

$$C^x/(E_2^x - E_1^x) = C^{st}/(E_2^{st} - E_1^{st})$$

In another embodiment of the present invention, the chromium atomic spectrometric signals are measured by flame atomic fluorescence spectrometric (FAFS) means. The flame is preferably low-temperature (such as propane-butane-air). In this embodiment, the flame serves to desolvate, volatilize, and atomize the analyte. Light from a light source provides photons that are absorbed by the analyte raising the analyte to an excited state. Increased radiation intensity causes an increase in chromium determination sensitivity. It is preferred that resonance fluorescence occurs, such that the wavelength of the fluoresced light is the same wavelength as the excitation light absorbed by the analyte, because this provides the best sensitivity. Light sources (including but not limited to hollow cathode lamps and lasers) would be selected to provide stable and intensive electromagnetic radiation in the spectral region where chromium resonance lines are located. Analogous to the FAAS process shown in FIG. 1A, chromium fluorescence signals $F_1^{st}$ (without added $HClO_4$) and $F_2^{st}$ (with added $HClO_4$) are measured for a solution of known Cr(III) concentration $C^{st}$. A calibration curve analogous to that shown in FIG. 1C may be generated if measurements are made for multiple concentrations. Analogous to the FAAS process shown in FIG. 1B chromium atomic fluorescence signals $F_1^x$ (without added $HClO_4$) and $F_2^x$ (with added $HClO_4$) are measured for the sample to be analyzed. The Cr(III) concentration $C^x$ may be determined from the calibration curve for the measured value of $\Delta F^x$. Alternatively, the sample Cr(III) concentration $C^x$ may be calculated from:

$$C^x/(F_2^x - F_1^x) = C^{st}/(F_2^{st} - F_1^{st})$$

In the various embodiments of the present invention described, the effective amounts of perchloric acid added to the sample and calibration standards are selected to cause an increase, preferably the maximum increase, in atomic spectrometric signal. The effective amounts of perchloric acid are preferably selected from the range of 0.3 to 10%, most preferably 0.3 to 1%. Increasing the amount of perchloric acid greater than 10% is permissible but deemed to be not expedient since it does not induce a further increase in the spectrometric signal. The preferred ranges of amounts of perchloric acid are based on 35% solution concentration, 4.35 molarity. If other concentrations are used, then the effective amount ranges may be adjusted by the factor (4.35/m) where m is the actual molarity.

In the various embodiments of the present invention described, the chromium absorption, emission and fluorescence signals are measured at wavelengths corresponding to the resonance spectral lines for chromium, preferably at a wavelength of 395.3 nm, 360.5 nm, 425.4 nm or 357.9 nm, most preferably at 357.9 nm.

The presence of $HNO_3$ does not change the pattern of increased spectrometric signal due to perchloric acid, allowing use of the invention with samples containing $HNO_3$. Samples are sometimes prepared with $HNO_3$, wherein the analyte is ashed or dissolved with $HNO_3$.

In the various embodiments of the present invention described, it is to be understood that various light sources may be used in the practice of the invention as is well known in the art, to provide light at the required wavelengths. Such light sources include, but are not limited to, various lamps such as spectral continuum sources and spectral line sources such as hollow cathode lamps, metal vapor lamps and electrodeless discharge lamps and lasers.

EXAMPLES

Example 1

FAAS

Nitric acid and then distilled water were added to dry bacterial samples. The volume of each sample was 6 ml. Each sample was divided into two equal parts. 100 µl of distilled water were added to one part. 100 µl of perchloric acid (solution density=1.25 kg/l, 35% solution, 4.35 molarity) were added to the second part. The two parts were each nebulized, flame (propane-butane-air) desolvated, volatilized and atomized; and the respective atomic absorbance signals measured at 357.9 nm using a Beckman 495 atomic absorption spectrometer, with a hollow cathode lamp (LCP-1, Russia) as the light source. A calibration standard was developed using Cr(III) concentrations of 3.2 µg/ml, 6.4 µg/ml, 12.8 µg/ml, and 25.6 µg/ml. The sample Cr(III) concentrations were determined by taking the difference of $A_2 - A_1$, where $A_1$ and $A_2$ were the values of atomic absorbance signals for the two parts, and compared to the measured difference for the calibration standard. Measured sample concentrations were in the range from 3.2 to 25.6 µg/ml.

Example 2

FAES

Nitric acid and then distilled water are added to a dry bacterial sample. The volume of sample is 6 ml. This sample is divided into two equal parts. 100 µl of distilled water is added to one part. 100 µl of perchloric acid (solution density=1.25 kg/l, 35% solution, 4.35 molarity) is added to the second part. The two parts are each nebulized; flame (propane-butane-air) desolvated, volatilized, atomized, and the chromium atoms excited to a higher energy state; and the respective atomic emittance signals measured at 357.9 nm. A calibration standard is developed using various known Cr(III) concentrations. The sample Cr(III) concentration is determined by taking the difference of $E_2 - E_1$, where $E_1$ and $E_2$ are the values of atomic emittance signals for the two parts and comparing to the measured difference for the calibration standard.

Example 3

FAFS

Nitric acid and then distilled water were added to dry bacterial samples. The volume of each sample was 6 ml. Each sample was divided into two equal parts. 100 µl of distilled water were added to one part. 1001 µl of perchloric acid (solution density=1.25 kg/l, 35% solution, 4.35 molarity) were added to the second part. The two parts were each nebulized; and flame (propane-butane-air) desolvated, volatilized, atomized. The chromium atoms were excited to a higher energy state by absorption of photons from a hollow cathode lamp (LCP-1, Russia; modulated at frequency of 350 Hz), and the respective atomic fluorescence signals measured at 357.9 nm. A photo multiplier (FEU 71, Russia) was used as a photoreceiver. An electric signal from the photoreceiver was passed to the multiplier and then to the synchronous detector (SD 9, Russia). A calibration standard was developed using Cr(III) concentrations of 6.4 µg/ml, 12.8 µg/ml, 25.6 µg/ml and 51.2 µg/ml. Sample Cr(III) concentrations were determined by taking the difference of $F_2-F_1$, where $F_1$ and $F_2$ were the values of atomic fluorescence signals for the two parts and compared to the measured difference for the calibration standard.

Obviously numerous modifications and variations of the present invention are possible in the light of the above teachings. It is therefore to be understood that within the scope of the appended claims the invention may be practiced otherwise than as specifically described therein.

What is claimed is:

1. A method for determination of the concentration of trivalent chromium Cr(III) in a sample (in solution) comprising the steps of:
dividing said sample into two sample parts;
adding a first effective amount of perchloric acid to said second sample part, sufficient to induce an increase in the chromium atomic absorption signal due to Cr(III);
measuring the chromium atomic absorption signals $A_1^x$ and $A_2^x$ from said first and second sample parts by flame atomic absorption spectrometry;
dividing a standard (in solution) of known Cr(III) concentration into two standard parts;
adding a second effective amount of perchloric acid to said second standard part, sufficient to induce an increase in the chromium atomic absorption signal due to Cr(III);
measuring the chromium atomic absorption signals $A_1^{st}$ and $A_2^{st}$ from said first and second standard parts by flame atomic absorption spectrometry;
determining the Cr(III) concentration in said sample by comparing the difference in measured signals for said sample to the measured difference for said standard.

2. The method of claim 1 further comprising the steps of:
adding an equal amount of transparent, non-reactive liquid about equal to amount of perchloric acid added to said second sample part to said first sample part prior to said sample absorption signal measuring step;
and adding an equal amount of transparent, non-reactive liquid about equal to amount of perchloric acid added to said second standard part to said first standard part prior to said standard absorption signal measuring step.

3. The method of claim 1 wherein:
said chromium atomic absorption signals are measured at a wavelength selected from the group consisting of 357.9, 360.5, 395.3 and 425.4 nm.

4. The method of claim 3 wherein:
said chromium atomic absorption signals are measured at a wavelength of 357.9 nm.

5. The method of claim 1 wherein:
said first and second effective amounts of perchloric acid are selected from the range of 0.3 to 10%, adjusted by the factor 4.35/M where M is the perchloric acid molarity.

6. The method of claim 5 wherein:
said first and second effective amounts of perchloric acid are selected from the range of 0.3 to 1%, adjusted by the factor 4.35/M where M is the perchloric acid molarity.

7. The method of claim 1 wherein:
said atomic absorption signal is the absorbance of chromium.

8. A method for determination of the concentration of trivalent chromium Cr(III) in a sample (in solution) comprising the steps of:
dividing said sample into two sample parts;
adding a first effective amount of perchloric acid to said second sample part, sufficient to induce an increase in the chromium atomic emittance signal due to Cr(III);
measuring the chromium atomic emittance signals $E_1^x$ and $E_2^x$ from said first and second sample parts by flame atomic emission spectrometry;
dividing a standard (in solution) of known Cr(III) concentration into two standard parts;
adding a second effective amount of perchloric acid to said second standard part, sufficient to induce an increase in the chromium atomic emittance signal due to Cr(III);
measuring the chromium atomic emittance signals $E_1^{st}$ and $E_2^{st}$ from said first and second standard parts by flame atomic emission spectrometry;
determining the Cr(III) concentration in said sample by comparing the difference in measured signals for said sample to the measured difference for said standard.

9. The method of claim 8 further comprising the steps of:
adding an equal amount of transparent, non-reactive liquid about equal to amount of perchloric acid added to said second sample part to said first sample part prior to said sample emittance signal measuring step;
and adding an equal amount of transparent, non-reactive liquid about equal to amount of perchloric acid added to said second standard part to said first standard part prior to said standard emittance signal measuring step.

10. The method of claim 8 wherein:
said chromium atomic emittance signals are measured at a wavelength selected from the group consisting of 357.9, 360.5, 395.3 and 425.4 nm.

11. The method of claim 10 wherein:
said chromium atomic emittance signals are measured at a wavelength of 357.9 nm.

12. The method of claim 8 wherein:
said first and second effective amounts of perchloric acid are selected from the range of 0.3 to 10%, adjusted by the factor 4.35/M where M is the perchloric acid molarity.

13. The method of claim 12 wherein:
said first and second effective amounts of perchloric acid are selected from the range of 0.3 to 1%, adjusted by the factor 4.35/M where M is the perchloric acid molarity.

14. A method for determination of the concentration of trivalent chromium Cr(III) in a sample (in solution) comprising the steps of:
dividing said sample into two sample parts;
adding a first effective amount of perchloric acid to said second sample part, sufficient to induce an increase in the chromium atomic fluorescence signal due to Cr(III);
measuring the chromium atomic fluorescence signals $F_1^x$ and $F_2^x$ from said first and second sample parts by flame atomic fluorescence spectrometry;
dividing a standard (in solution) of known Cr(III) concentration into two standard parts;
adding a second effective amount of perchloric acid to said second standard part, sufficient to induce an increase in the chromium atomic fluorescence signal due to Cr(III);
measuring the chromium atomic fluorescence signals $F_1^{st}$ and $F_2^{st}$ from said first and second standard parts by flame atomic fluorescence spectrometry;
determining the Cr(III) concentration in said sample by comparing the difference in measured signals for said sample to the measured difference for said standard.

15. The method of claim 14 further comprising the steps of:
adding an equal amount of transparent, non-reactive liquid about equal to amount of perchloric acid added to said second sample part to said first sample part prior to said sample fluorescence signal measuring step;
and adding an equal amount of transparent, non-reactive liquid about equal to amount of perchloric acid added to said second standard part to said first standard part prior to said standard fluorescence signal measuring step.

16. The method of claim 14 wherein:
said chromium atomic fluorescence signals are measured at a wavelength selected from the group consisting of 357.9, 360.5, 395.3 and 425.4 nm.

17. The method of claim 16 wherein:
said chromium atomic fluorescence signals are measured at a wavelength of 357.9 mm.

18. The method of claim 14 wherein:
said first and second effective amounts of perchloric acid are selected from the range of 0.3 to 10%, adjusted by the factor 4.35/M where M is the perchloric acid molarity.

19. The method of claim 18 wherein:
said first and second effective amounts of perchloric acid are selected from the range of 0.3 to 1%, adjusted by the factor 4.35/M where M is the perchloric acid molarity.

* * * * *